US012673917B2

(12) United States Patent
Maher et al.

(10) Patent No.: US 12,673,917 B2
(45) Date of Patent: Jul. 7, 2026

(54) BISPHENOLS BEARING PENDANT CLICKABLE NORBORNENYL GROUP AND POLYMERS THEREFROM

(71) Applicant: COUNCIL OF SCIENTIFIC & INDUSTRIAL RESEARCH, New Delhi (IN)

(72) Inventors: Deepak Mannusing Maher, Pune (IN); Samadhan Suresh Nagane, Pune (IN); Prakash Purushottam Wadgaonkar, Pune (IN)

(73) Assignee: COUNCIL OF SCIENTIFIC & INDUSTRIAL RESEARCH (IN)

( * ) Notice: Subject to any disclaimer, the term of this patent is extended or adjusted under 35 U.S.C. 154(b) by 405 days.

(21) Appl. No.: 18/259,365

(22) PCT Filed: Dec. 29, 2021

(86) PCT No.: PCT/IN2021/051214
§ 371 (c)(1),
(2) Date: Jun. 26, 2023

(87) PCT Pub. No.: WO2022/144921
PCT Pub. Date: Jul. 7, 2022

(65) Prior Publication Data

US 2024/0083849 A1 Mar. 14, 2024

(30) Foreign Application Priority Data

Dec. 30, 2020 (IN) ............................. 202011057103

(51) Int. Cl.
*C07D 209/46* (2006.01)
*C08G 63/685* (2006.01)
*C08G 63/81* (2006.01)

(52) U.S. Cl.
CPC ....... *C07D 209/46* (2013.01); *C08G 63/6856* (2013.01); *C08G 63/81* (2013.01)

(58) Field of Classification Search
None
See application file for complete search history.

(56) References Cited

U.S. PATENT DOCUMENTS

| | | | |
|---|---|---|---|
| 5,344,910 | A | 9/1994 | Sybert |
| 7,365,124 | B2 | 4/2008 | Srinivasan et al. |
| 9,676,716 | B2 | 6/2017 | Heuer et al. |
| 9,822,070 | B2 | 11/2017 | Bhotla et al. |
| 10,239,865 | B2 | 3/2019 | Nagane et al. |
| 2005/0228137 | A1 | 10/2005 | Srinivasan et al. |
| 2011/0151262 | A1 | 6/2011 | Heuer et al. |
| 2016/0340307 | A1 | 11/2016 | Bhotla et al. |
| 2018/0009788 | A1 | 1/2018 | Nagane et al. |

FOREIGN PATENT DOCUMENTS

| | | | |
|---|---|---|---|
| EP | 0617070 | A2 | 9/1994 |
| EP | 1582549 | A1 | 10/2005 |
| EP | 2338880 | B1 | 6/2011 |

(Continued)

OTHER PUBLICATIONS

Notification of Transmittal of the International Search Report and the Written Opinion of the International Searching Authority, issued in PCT/IN2021/051214 on Mar. 21, 2022.
International Search Report issued in PCT/IN2021/051214, on Mar. 21, 2022.
Written Opinion issued in PCT/IN2021/051214, on Mar. 21, 2022.
Lin M S et al, "Polymers with improved flammability characteristics. I. Phenolphthalein-related homopolymers", Journal of Polymer Science Part A: Polymer Chemistry, John Wiley & Sons, Inc, US, vol. 19, Jan. 1, 1981; p. 2659-2670.

*Primary Examiner* — Samantha L Shterengarts
(74) *Attorney, Agent, or Firm* — The Belles Group, P.C.

(57) ABSTRACT

The present invention relates to a new bisphenol bearing pendant clickable norbornenyl group of formula (I) and its aromatic polyesters bearing pendant norbornenyl groups of formula (II) and processes for the preparation thereof.

Formula (I)

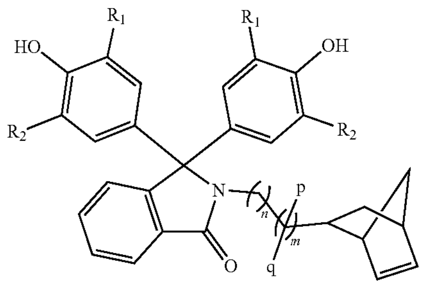

Formula (II)

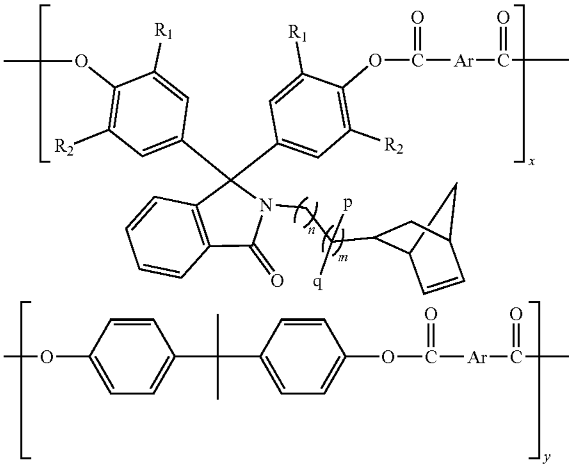

7 Claims, 4 Drawing Sheets

(56) References Cited

FOREIGN PATENT DOCUMENTS

| | | | |
|---|---|---|---|
| WO | 2015107467 | A1 | 7/2015 |
| WO | 2016113760 | A1 | 7/2016 |

(a) (b)

BISPHENOLS BEARING PENDANT CLICKABLE NORBORNENYL GROUP AND POLYMERS THEREFROM

CROSS-REFERENCE TO RELATED PATENT APPLICATIONS

The present application is a U.S. national stage application under 35 U.S.C. § 371 of PCT/IN2021/051214, filed Dec. 29, 2021, which claims priority to Indian Patent Application number 202011057103 filed on Dec. 30, 2020. The disclosures of the aforementioned priority applications are incorporated herein by reference.

FIELD OF THE INVENTION

The present invention relates to a new bisphenol bearing pendant clickable norbornenyl group and polymers therefrom. More particularly, the present invention relates to a new bisphenol bearing pendant clickable norbornenyl group of formula (I) and aromatic polyesters bearing pendant norbornenyl groups of formula (II) and processes for the preparation thereof.

BACKGROUND AND PRIOR ART OF THE INVENTION

Bisphenols are the building blocks for a range of industrially relevant polymers such as aromatic polycarbonates, polyesters, poly(arylene ether)s, cyanate esters, epoxy resins, etc. Therefore, there is a strong interest in the design and synthesis of new bisphenols with special structural features. Bisphenols containing pendant (clickable) functional groups are particularly attractive as they provide access to step-growth polymers fitted with pendant reactive functional groups which could subsequently be post-modified with appropriate reagents. Bisphenols possessing pendant clickable functional groups such as open chain alkene, propargyloxy, azido, furyl or maleimide are known in the literature. However, bisphenols bearing pendant cyclo-alkene group such as norbornenyl are scarce except for 1,4-dihydro-1,4-methanonaphthalene-5,8-diol.

Polymers possessing pendant or end-standing norbornenyl group(s) are valuable precursors for various macromolecular architectures such as graft copolymers, block copolymers, cross-link polymers, etc as reactive alkene functional group in norbornenyl moiety is capable of undergoing a set of interesting click reactions such as tetrazine-norbornene inverse electron demand Diels-Alder reaction, photoinitiated thiol-norbornene reaction, metal-free azide-norbornene 1,3-dipolar cycloaddition reaction and so on. Polymers bearing pendant norbornenyl groups have been synthesized via the following routes: A) ring-opening polymerization of cyclic monomers containing norbornenyl group B) step growth polymerization of monomers bearing pendant norbornenyl group and C) chemical modification of preformed polymers using appropriate norbornenyl-containing reagents.

Therefore, there is a need in the art to provide such bisphenol bearing pendant norbornenyl groups and their polymers. There is also a need to provide cheap, simple and industrially applicable process for the preparation of these compounds.

OBJECTS OF THE INVENTION

The main objective of the present invention is to provide a new bisphenol bearing pendant clickable norbornenyl group of formula (I) and process for the preparation thereof.

Yet another objective of the present invention is to provide aromatic polyesters bearing pendant norbornenyl groups of formula (II) from a new bisphenol bearing pendant clickable norbornenyl group and process for the preparation thereof.

Still another objective of the present invention is to provide a post-modified polymer of polymers possessing pendant norbornenyl groups of formula (II) and process for the preparation thereof.

SUMMARY OF THE INVENTION

Accordingly, to accomplish the objectives, the present invention provides a new bisphenol bearing pendant clickable norbornenyl group of formula (I) and its aromatic polyesters bearing pendant norbornenyl groups of formula (II), and processes for the preparation thereof.

In an embodiment, the present invention provides a new bisphenol bearing pendant clickable norbornenyl group of formula (I) below:

Formula (I)

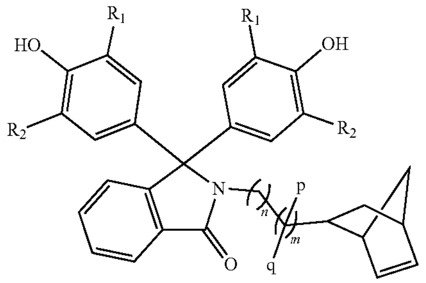

wherein, $R_1$ and $R_2$ are selected from the group comprising of H, $C_1$-$C_5$ substituted or unsubstituted, straight or branched alkyl, alkoxy;

p and q are selected form the group comprising of H and F;

m=0 or 1; n=0-6.

Another embodiment of the present invention provides a process for the preparation of a new bisphenol bearing pendant clickable norbornenyl group of formula (I), wherein said process comprises of stirring the reaction mixture comprising of primary alkyl amine possessing norbornenyl, compound (2), and phenolphthalein derivative, compound (1), in the molar ratio ranging between 10:1 to 25:1 for a period in the range of 30 to 60 h at a temperature in the range of 120° C. to 160° C. to afford bisphenol of formula (I).

One more embodiment of the present invention provides aromatic polyesters bearing pendant norbornenyl groups of formula (II) from a new bisphenol bearing pendant clickable norbornenyl group of formula (I).

Formula (II)

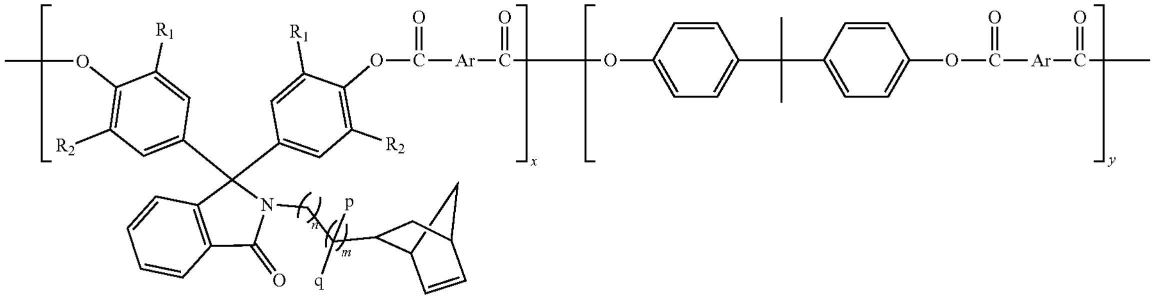

wherein, $R_1$ and $R_2$ are selected from the group comprising of H, $C_1$-$C_5$ substituted or unsubstituted, straight or branched alkyl, alkoxy;

p and q are selected form the group comprising of H and F;

m=0 or 1; n=0-6;

wherein, x=0.1-1, and y=0-0.9;

Ar=isophthaloyl chloride, terephthaloyl chloride, or mixtures thereof.

Yet another embodiment of the present invention provides a process for the preparation of polyester of formula (II), wherein said process comprises the steps of:

a) dissolving monomer of formula (I) and/or bisphenol A in an alkali solution and stirring the reaction mixture;
b) adding benzyltriethylammonium chloride to the reaction mixture of step (a) and stirring followed by addition of a solution of diacid chloride in dichloromethane to the reaction mixture and stirring vigorously; and
c) pouring the reaction mixture of step (b) into hot water; filtering the precipitated polymer and washing it several times with water followed by work-up to afford polyester of formula (II).

In another embodiment of the present invention, polymers of formula (II) possessing pendant norbornenyl groups are capable of undergoing tetrazine-norbornene inverse electron demand Diels-Alder reaction, photoinitiated thiol-norbornene reaction or metal-free azide-norbornene 1,3-dipolar cycloaddition click reaction to form post-modified polymers. Polymers bearing pendant norbornenyl groups of formula (II) could be cross-linked thermally or photochemically.

DETAILED DESCRIPTION OF THE INVENTION

Figure 1:
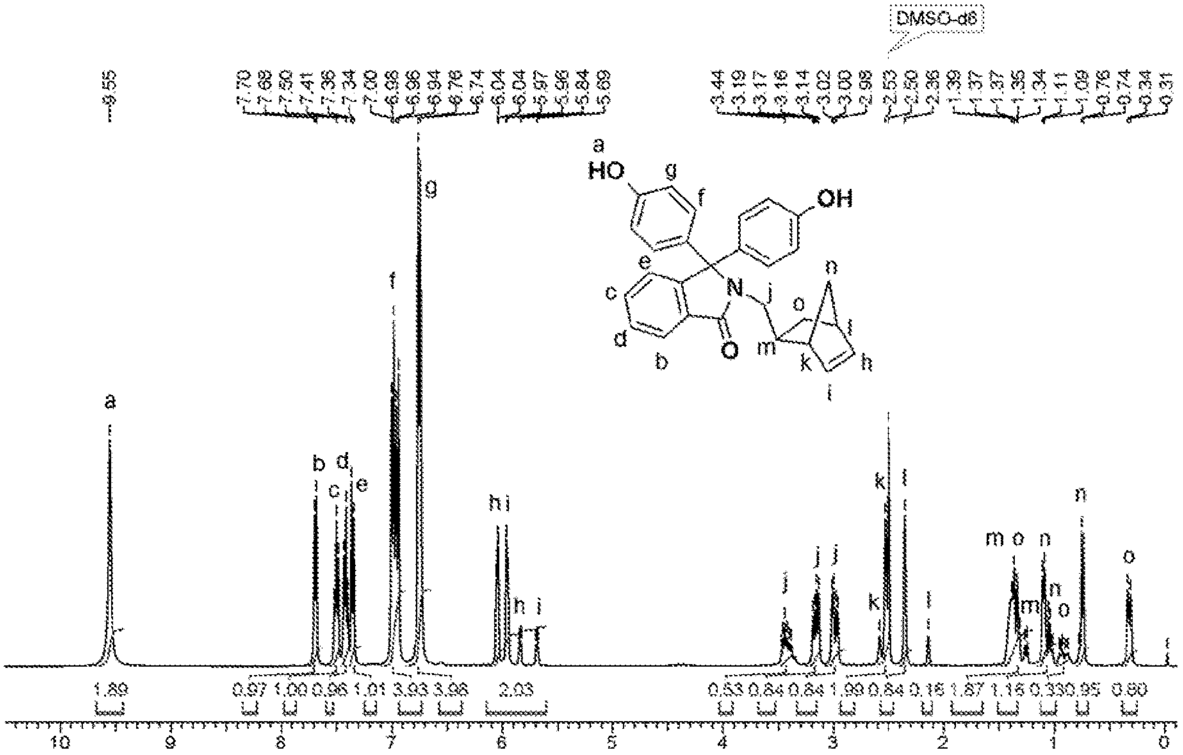
FIG. 1: illustrates $^1$H-NMR spectrum (in DMSO-$d_6$) of 2-(bicycle [2.2.1] hept-5-en-2-ylmethyl) 3,3-bis (4-hydroxyphenyl) isoindolin-1-one, (Monomer-1)

It is to be understood that the figures and descriptions of the present invention have been simplified to illustrate elements that are relevant for a clear understanding of the invention. The detailed description will be provided herein below with reference to the attached drawing.

The present invention provides a new bisphenol bearing pendant clickable norbornenyl group of formula (I) and its aromatic polyesters bearing pendant norbornenyl groups of formula (II), and processes for the preparation thereof.

In an embodiment, the present invention provides a new bisphenol bearing pendant clickable norbornenyl group of formula (I) below:

Formula (I)

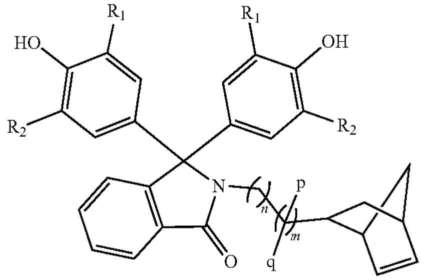

wherein, $R_1$ and $R_2$ are selected from the group comprising of H, $C_1$-$C_5$ substituted or unsubstituted, straight or branched alkyl, alkoxy;

p and q are selected form the group comprising of H and F;

m=0 or 1; n=0-6.

Another embodiment of the present invention provides a process for the preparation of a new bisphenol bearing pendant clickable norbornenyl group of formula (I), wherein said process comprises of stirring the reaction mixture comprising of primary alkyl amine possessing norbornenyl group, compound (2), and phenolphthalein derivative, compound (1), in the molar ratio ranging between 10:1 to 25:1 for the period in the range of 30 to 60 hours at a temperature in the range of 120° C. to 160° C. to afford bisphenol of formula (I). The general process depicted below in scheme-1:

Scheme-1

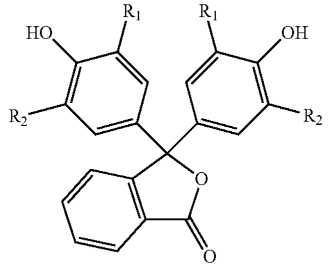

+

Compound-1

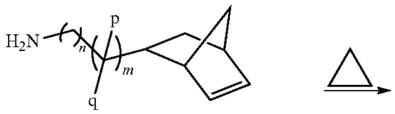

Compound-2

-continued

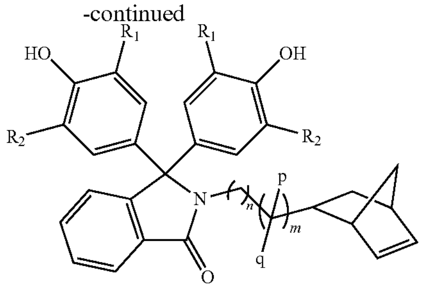

Formula-I wherein, $R_1$ and $R_2$ are selected from the group comprising of H, $C_1$-$C_5$ substituted or unsubstituted, straight or branched alkyl, alkoxy;

p and q are selected form the group comprising of H and F;

m=0 or 1; n=0-6.

One more embodiment of the present invention provides an aromatic polyester bearing pendant norbornenyl groups of formula (II) from a new bisphenol bearing pendant clickable norbornenyl group of formula (I).

Formula (II)

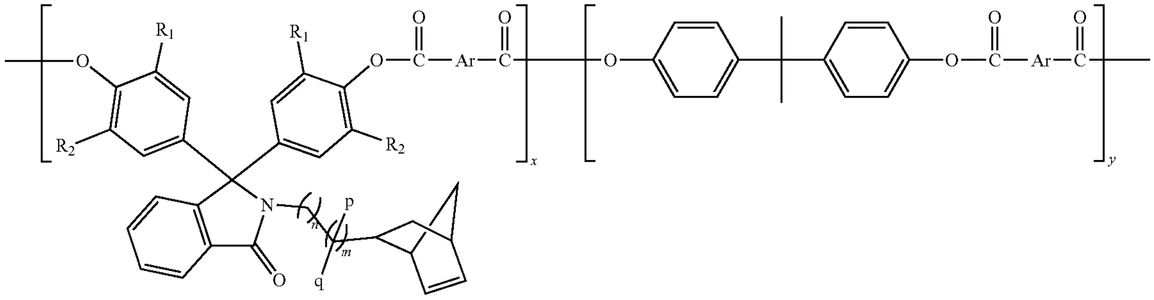

wherein, $R_1$ and $R_2$ are selected from the group comprising of H, $C_1$-$C_5$ substituted or unsubstituted, straight or branched alkyl, alkoxy;

p and q are selected form the group comprising of H and F;

m=0 or 1; n=0-6;

wherein, x=0.1-1, and y=0-0.9;

Ar=isophthaloyl chloride, terephthaloyl chloride, or mixtures thereof.

Yet another embodiment of the present invention provides a process for the preparation of polyester of formula (II), wherein said process comprises the steps of:

a) dissolving monomer of formula (I) and/or bisphenol A in an alkali solution and stirring the reaction mixture;

b) adding benzyltriethylammonium chloride to the reaction mixture of step (a) and stirring followed by addition of a solution of diacid chloride in dichloromethane to the reaction mixture and stirring vigorously; and c) pouring the reaction mixture of step (b) into hot water; filtering the precipitated polymer and washing it several times with water followed by work-up to afford polyester of formula (II).

Diacid chloride is selected from isophthaloyl chloride, terephthaloyl chloride, or mixtures thereof.

The general process for the preparation of polyester of formula (II) is depicted below in scheme-2:

Scheme-2

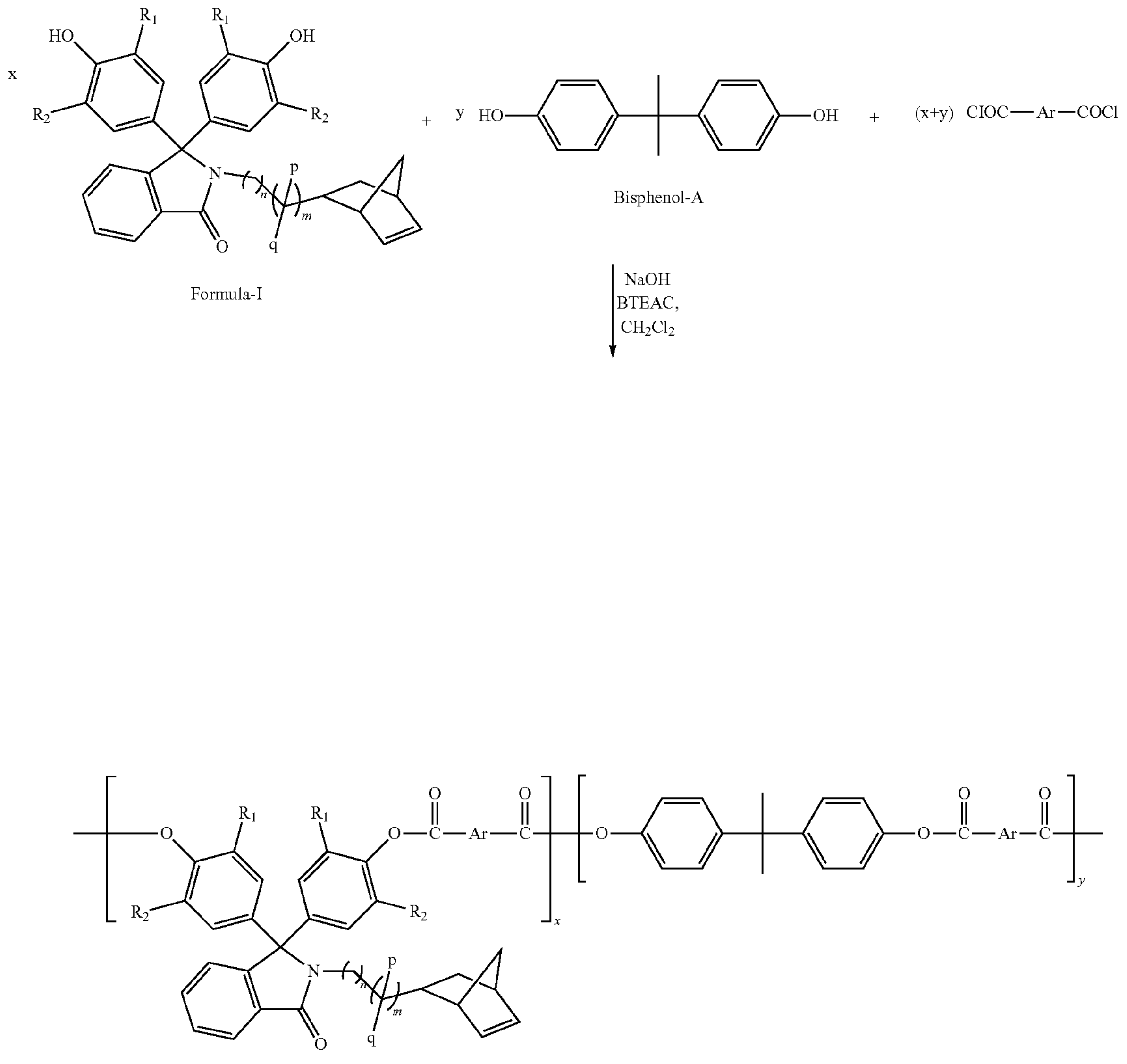

Formula-I

Bisphenol-A

Formula (II)

wherein, $R_1$ and $R_2$ are selected from the group comprising of H, $C_1$-$C_5$ substituted or unsubstituted, straight or branched alkyl, alkoxy;

p and q are selected form the group comprising of H and F;

m=0 or 1; n=0-6;

wherein, x=0.1-1, and y=0-0.9;

Ar=isophthaloyl chloride, terephthaloyl chloride, or mixtures thereof.

In another embodiment of the present invention, polymers of formula (II) possessing pendant norbornenyl groups are capable of undergoing tetrazine-norbornene inverse electron demand Diels-Alder reaction, photoinitiated thiol-norbornene reaction or metal-free azide-norbornene 1,3-dipolar cycloaddition click reaction to form post-modified polymers. Polymers bearing pendant norbornenyl groups of formula (II) could be cross-linked thermally or photochemically. The highly reactive strained ring of norbornenyl group provides a bundle of opportunities for post-modifications. For instance, norbornenyl group is capable of reacting with azides by heat-promoted 1,3-dipolar cycloaddition, the inverse electron demand Diels-Alder reaction with tetrazine and radical addition of thiols promoted by UV irradiation.

In preferred embodiment of the present invention, a representative copolyester bearing pendant norbornenyl groups are post-modified with tetrazine viz., 3,6-diphenyl-1,2,4,5-tetrazine via inverse electron demand Diels-Alder reaction. Norbornene-tetrazine click reaction is utilized as a tool for chemical modification. A representative copolyester bearing pendant norbornenyl groups polymer-2 was reacted with 1.5 equivalents of 3,6-diphenyl-1,2,4,5-tetrazine at a temperature in the range of 25-30° C. for 6 hours in dichloromethane as a solvent to get modified polymer of formula (A). Reaction is depicted below in scheme-4.

Scheme-4

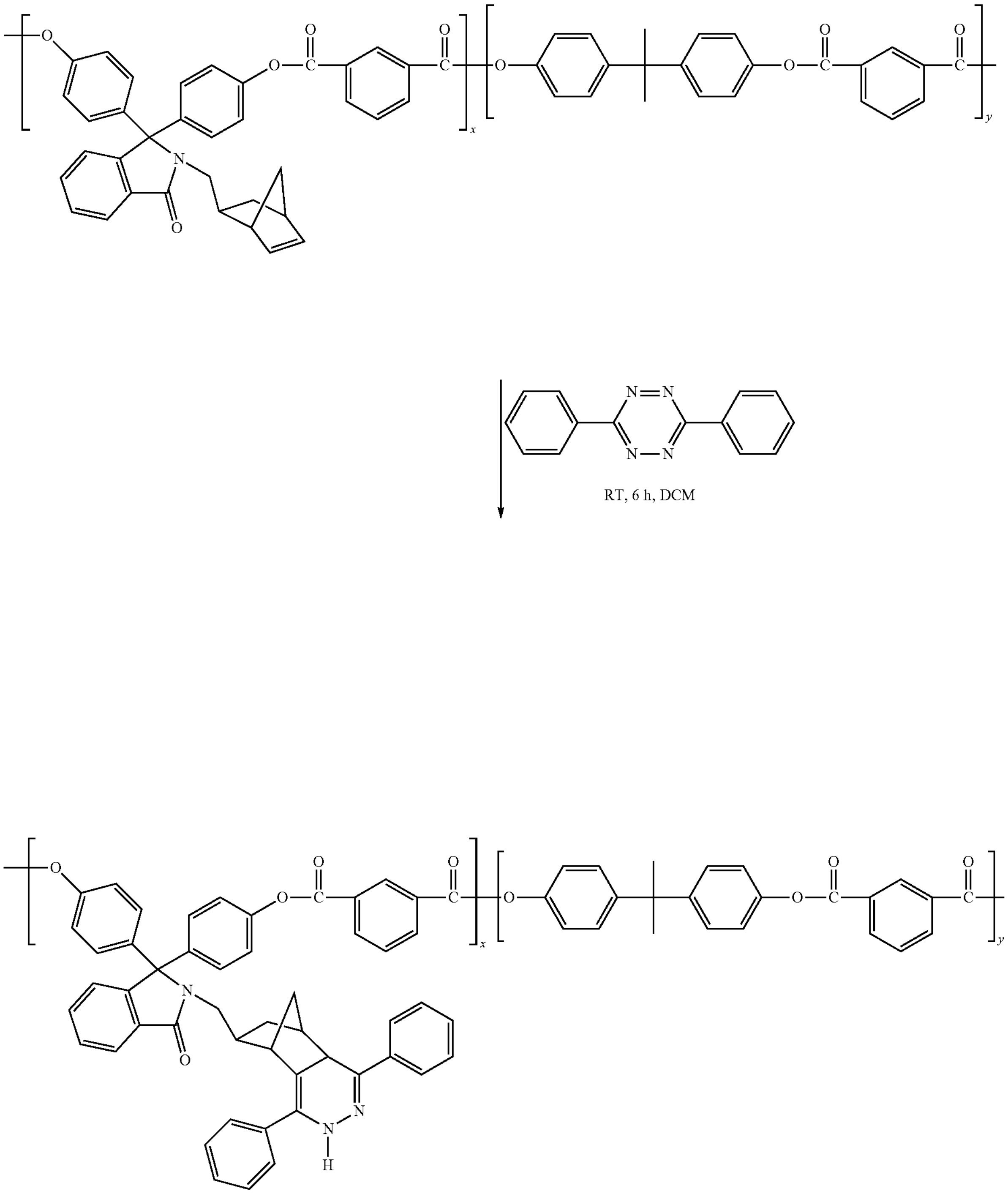

(A)

Figure 4:
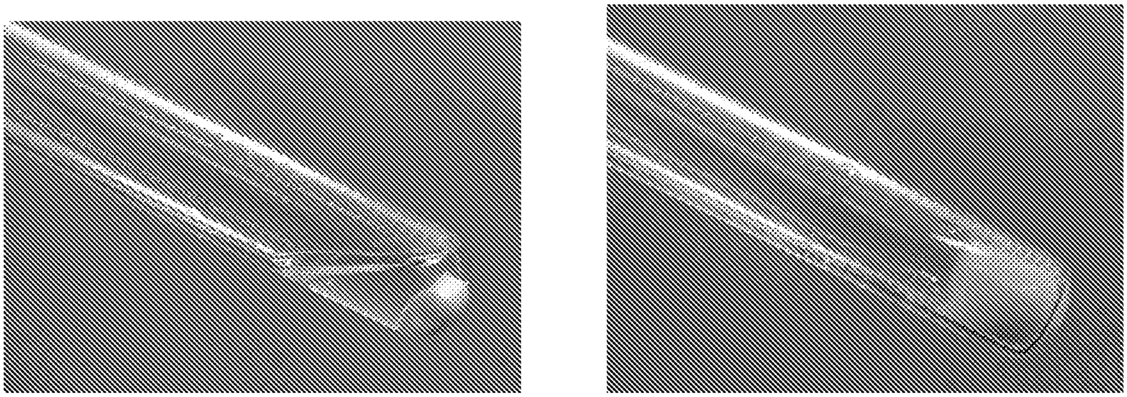
FIG. 4: (a): illustrates reaction of copolyester polymer-2 dissolved in DMF with 25 mol % PETMP in the presence of DMPA (5 mol % relative to thiol) as a photoinitiator. (b): illustrates exposure of the reaction mixture to 365 nm light at a temperature in the range of 25-30° C. for 1 minute when the homogeneous solution turned into a cross-linked polymer.

After successful post-modification of aromatic copolyester via norbornene-tetrazine click reaction, the efficacy of reaction of pendant norbornenyl groups towards norbornene-thiol click reaction is investigated using a multifunctional thiol as shown in Scheme-5. In a representative example, copolyester, polymer-2, dissolved in DMF was reacted with 25 mol % tetrakis (3-mercapto propionate) (PETMP) in the presence of DMPA (5 mol % relative to thiol) as a photoinitiator (FIG. 4(*a*)). The reaction mixture was exposed to 365 nm light at a temperature in the range of 25-30° C. for 1 minute when the homogeneous solution turned into a cross-linked polymer (B) as depicted in FIG. 4(*b*).

Scheme-5

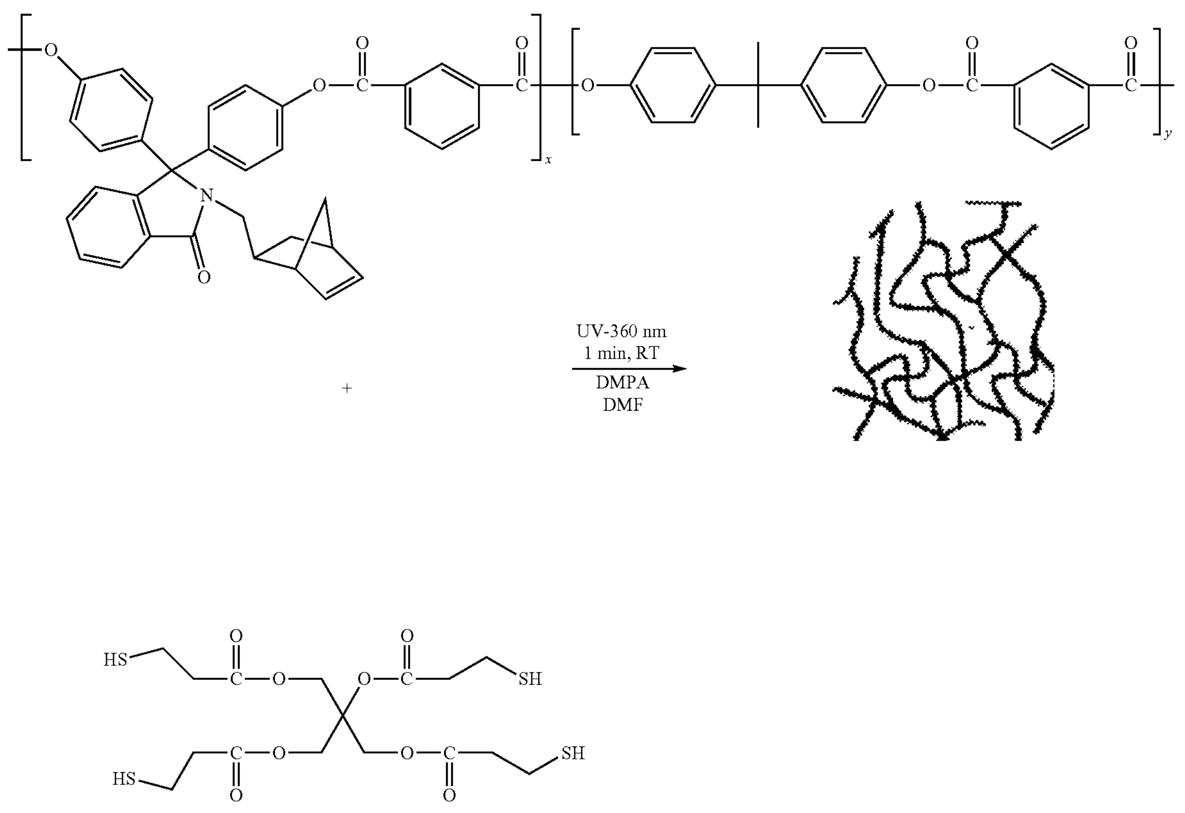

EXAMPLES

Following examples are given by way of illustration and therefore should not be construed to limit the scope of the invention.

Example 1: General Process for the Preparation of Bisphenol of Formula (I)

Into a 250 mL two-necked round bottom flask equipped with a reflux condenser were charged phenolphthalein derivative of compound (1) (1.0 eq) and compound of compound (2) (a mixture of endo and exo isomers 80:20 mol %) (12.0 eq) and the reaction mixture was heated under stirring at 150° C. for 48 hours. The excess compound of compound (2) was removed under reduced pressure. The reaction mixture was cooled to 30° C. and dissolved in ethyl acetate and the solution was washed with water. The ethyl acetate layer was separated, dried over anhydrous sodium sulfate, filtered and ethyl acetate was removed under reduced pressure at 30° C. The crude product was dissolved in aqueous sodium hydroxide solution and the solution was acidified with dilute hydrochloric acid. The precipitated product was separated out by filtration and washed with cold water. The product was recrystallized from a mixture of ethanol:water (1:1, v/v) to afford of bisphenol of formula (I).

Monomer-1: 2-(bicycle [2.2.1] hept-5-en-2-ylm-ethyl)-3,3-bis (4-hydroxyphenyl) isoindolin-1-one (BPN)

Monomer-1

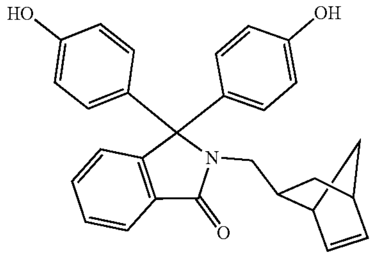

White crystals: Yield: 10.65 g (80%); Melting point: >300° C.; FT-IR (KBr, $cm^{-1}$): 3385, 2960, 1636, 1502; $^1H$ NMR (400 MHz, DMSO-$d_6$, δ/ppm) (FIG. 1)=9.55 (br. s., 2H), 7.69 (d, 1H), 7.50 (t, 1H), 7.41 (t, 1H), 7.35 (d, 1H), 7.00-6.94 (m, 4H), 6.75 (d, 4H), 6.06-5.68 (m, 2H), 3.48-2.97 (m, 2H), 2.55 (d, 2H), 2.36-2.15(d, 1H), 1.39-1.25 (m, 2H), 1.11-1.02 (m, 1H), 0.93-0.74 (m, 1H), 3.33 (d, 1H); $^{13}C$ NMR (DMSO-$d_6$, δ/ppm): 167.8, 167.4, 157.2, 157.0, 151.9, 136.8, 136.4, 136.2, 132.8, 132.1, 130.9, 130.7 130.2, 130.1, 129.5, 129.3, 129.2, 129.0, 127.8, 132.5, 122.7, 115.3, 74.7, 49.1, 44.8, 44.5, 44.0, 41.9, 41.1, 37.6, 37.2, 30.6.

Example 2: General Process for the Preparation of Polyester of Formula (II)

An oven-dried, 100 mL two-necked round bottom flask equipped with a high-speed mechanical stirrer and an addition funnel was charged with formula (I) (1.0 eq) and 1 M aqueous solution of sodium hydroxide (2.0 eq). The reaction mixture was stirred at 10° C. for 1 hour. Thereafter, benzyltriethylammonium chloride (BTEAC) (0.06 eq) was added to the reaction mixture. The solution of isophthaloyl chloride (1.0 eq) dissolved in dichloromethane was added in one lot to the reaction mixture and the mixture was stirred vigorously at 2000 rpm for 1 hour. After completion of reaction time, the reaction mixture was poured into hot water, the precipitated polymer was filtered and washed with water. Polymer was dried and dissolved in dichloromethane and reprecipitated into mixture of methanol: water (1:1, v/v). The fibrous polymer was filtered, washed with methanol and dried at 50° C. under reduced pressure for 24 h.

Polymer-1

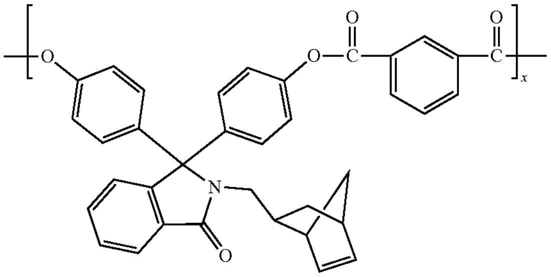

Synthesized Co-Polymer

Polymer-2

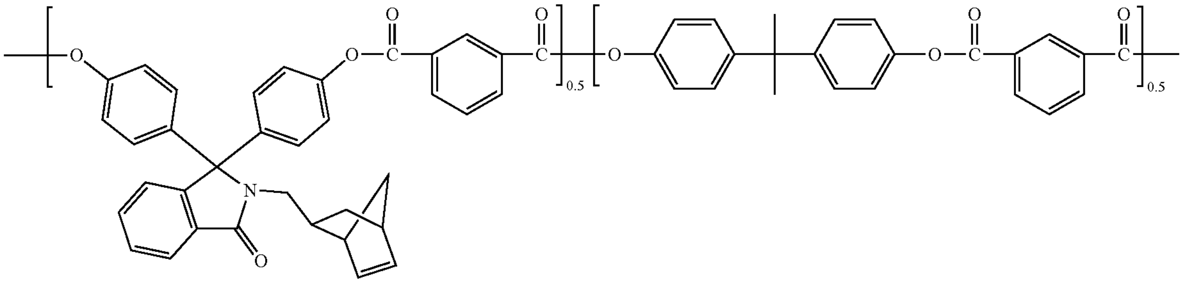

Figure 2:
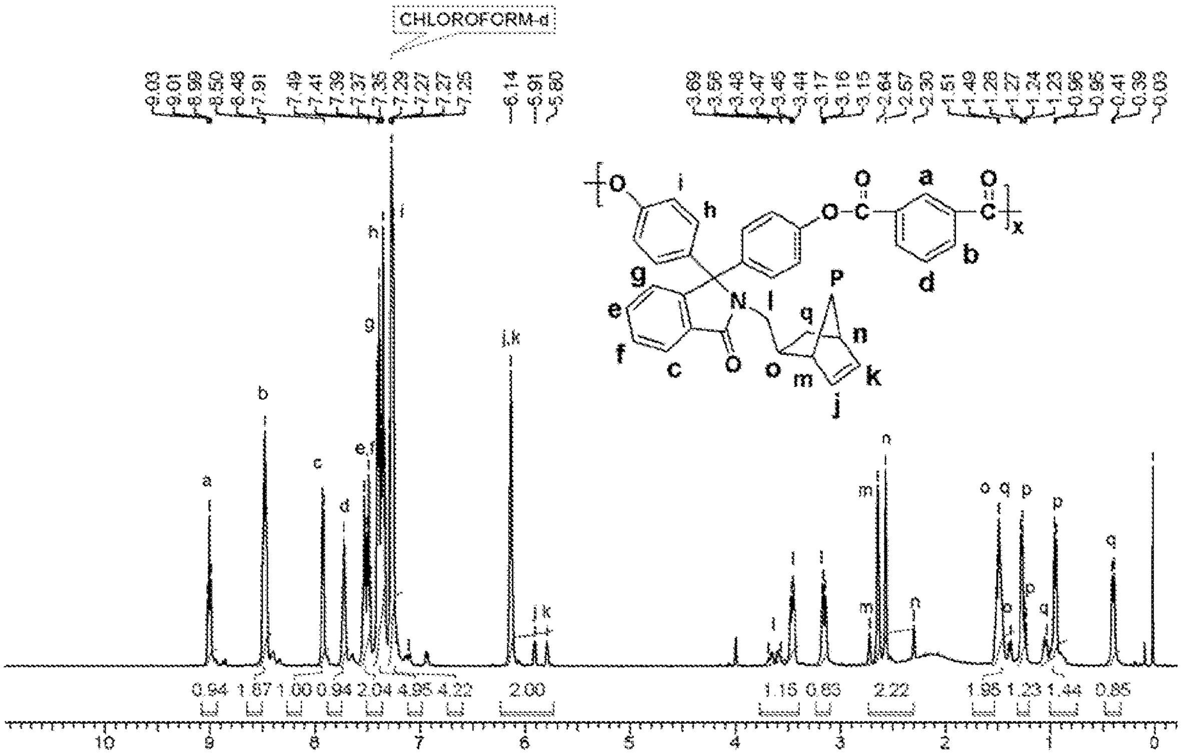
FIG. 2: illustrates $^1$H-NMR spectrum (in $CDCl_3$) of aromatic polyester, (polymer-1), obtained by polycondensation of 2-(bicycle [2.2.1] hept-5-en-2-ylmethyl) 3,3-bis (4-hydroxyphenyl) isoindolin-1-one with isophthaloyl chloride.
Figure 3:
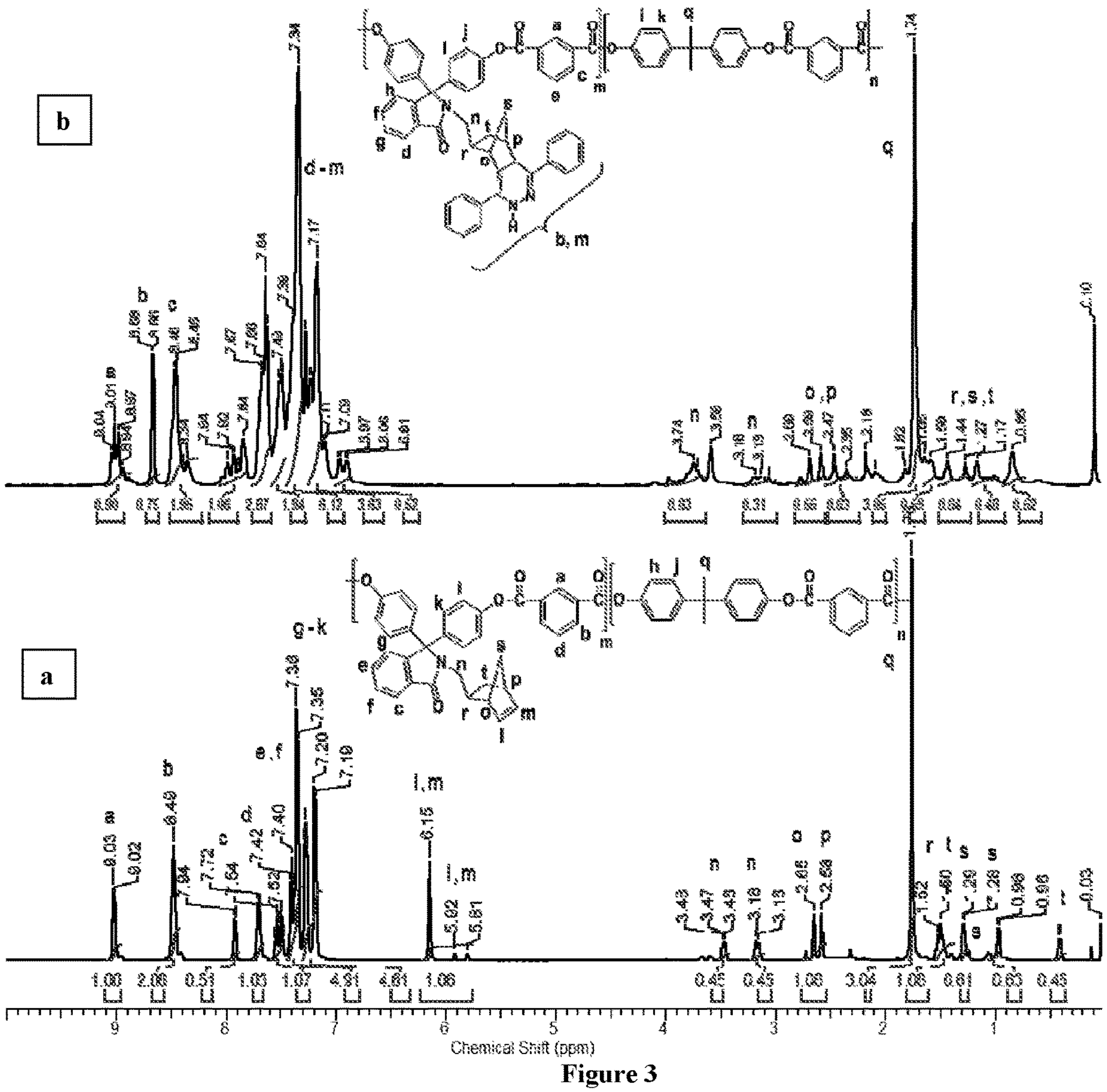
FIG. 3: illustrates $^1$H-NMR spectra of copolyester bearing pendant norbornenyl groups (polymer-2). (a) before post-modification, (b) after post modification via norbornene-tetrazine click reaction

FT-IR ($CHCl_3$, $cm^{-1}$): 2960, 1740, 1685, 1502; $^1H$ NMR (400 MHz, $CDCl_3$, δ/ppm) (FIG. 2)=9.01 (t, 1H), 8.49 (t, 1H), 7.93 (d, 1H), 7.74-7.71 (m, 1H), 7.55-7.48 (m, 2H), 7.41-7.34 (m, 5H), 7.27-7.25 (m, 4H), 6.14-6.50 (m, 2H), 3.67-3.15 (m, 2H), 2.72-2.30 (m, 2H), 1.51-1.38 (m, 2H), 1.29-1.24 (m, 1H), 1.06-0.95 (m, 2H), 0.40 (d, 1H), $^{13}C$ NMR ($CDCl_3$, δ/ppm): 168.7, 164.0, 150.7, 150.5, 150.4, 138.5, 138.3, 137.4, 135.1, 132.9, 132.3, 131.8, 130.7, 130.0, 129.8, 129.2, 128.5, 123.8, 123.3, 121.9, 75.1, 49.5, 45.6, 45.1, 42.4, 38.3, 31.1.

Example 3: Representative Process for the Preparation of Copolyester (50:50) of Formula (II) with Using Bisphenol-A as a Comonomer An oven-dried, 100 mL two-necked round bottom flask equipped with a high-speed mechanical stirrer and an addition funnel was charged with formula (I) (0.5) eq), bisphenol-A (0.5 eq) and 1 M aqueous solution of sodium hydroxide (2.0 eq). The reaction mixture was stirred at 10° C. for 1 hour. Thereafter, benzyltriethylammonium chloride (BTEAC) (0.06 eq) was added to the reaction mixture. The solution of isophthaloyl chloride (1.0 eq) dissolved in dichloromethane was added in one lot to the reaction mixture and the mixture was stirred vigorously at 2000 rpm for 1 hour. After completion of reaction time, the reaction mixture was poured into hot water, the precipitated polymer was filtered and washed with water. Polymer was dried and dissolved in dichloromethane and reprecipitated into mixture of methanol: water (1:1, v/v). The fibrous copolymer was filtered, washed with methanol and dried at 50° C. under reduced pressure for 24 hours. The copolyester is designated as polymer-2.

Copolyesters were synthesized by polycondensation of varying molar ratios of monomer-1 and BPA with IPC using the similar procedure. Copolyesters were designated as polymer-3 and polymer-4 wherein the feed % molar composition of monomer-1 and BPA was 30:70, and 10:90, respectively.

Example 4: Post-Modification of Polymer-2 Via Tetrazine-Norbornene Click Reaction In an oven-dried Schlenk tube were placed polymer-2 (100 mg, 2.19x10−3 mol), 3,6-diphenyl-1,2,4,5-tetrazine (103 mg, 4.39x10−3 mol) and dry DCM (1 mL). The reaction mixture was degassed by purging with nitrogen and stirred at room temperature for 6 hours. The reaction mixture was poured into methanol (25 mL) to precipitate the polymer. The precipitated polymer was filtered off and then dried under vacuum at room temperature for 8 h. The post-functionalized polymer was designated as polymer-2-Tz.

Polymer-2-Tz

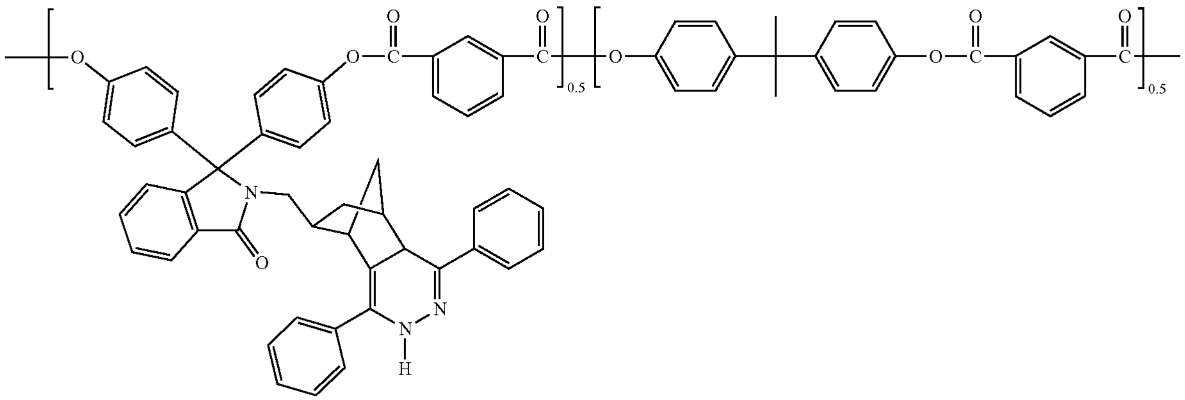

Example 5: Cross-Linking of Copolyester, Polymer-2, Via Thiol-Norbornene Click Reaction In an oven-dried Schlenk tube were placed polymer-2 (100 mg, $2.19\times10^{-3}$ mol), tetrakis (3-mercapto propionate (30 mg, $0.657\times10^{-3}$ mol), DMPA (5 mol % relative to thiol) and dry N,N-dimethyl formamide (1 mL). The reaction mixture was degassed by purging with nitrogen and then irradiated using a UV lamp at 365 nm for 1 minute to obtain the cross-linked polymer.

Advantages of the Invention

Bisphenols bearing pendant norbornenyl groups were readily synthesized starting from commercially available phenolphthalein via single-step reaction with primary alkyl amines possessing norbornenyl moiety These cardo bisphenols are potentially useful for the synthesis of aromatic polycarbonates, polyesters, poly (arylene ether)s, cyanate esters, epoxy resins, etc.

Polymers possessing pendant norbornenyl groups are capable of undergoing tetrazine-norbornene inverse electron demand Diels-Alder reaction, photoinitiated thiol-norbornene reaction or metal-free azide-norbornene 1,3-dipolar cycloaddition click reaction to form modified polymers Polymers bearing pendant norbornenyl groups could be cross-linked thermally or photochemically.

We claim:

1. A new bisphenol bearing pendant clickable norbornenyl group of formula (I) below:

Formula (I)

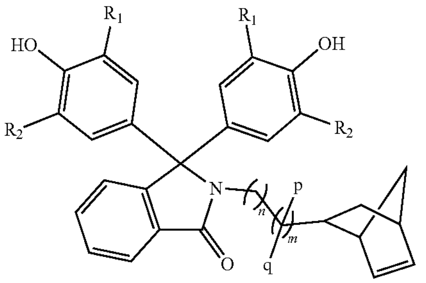

wherein, $R_1$ and $R_2$ are selected from a group comprising of H, $C_1$-$C_5$ substituted or unsubstituted, straight or branched alkyl, alkoxy; p and q are selected form a group comprising of H and F; m=0 or 1; n=0-6.

2. A process for the preparation of a new bisphenol bearing pendant clickable norbornenyl group of formula (I) as claimed in claim 1, wherein said process comprises of stirring the reaction mixture comprising of primary alkyl amine possessing norbornenyl group, compound (2), and phenolphthalein derivative, compound (1), in a molar ratio ranging between 10:1 to 25:1 for a period in a range of 30 to 60 hours at a temperature in a range of 120° C. to 160° C. to afford bisphenol of formula (I);

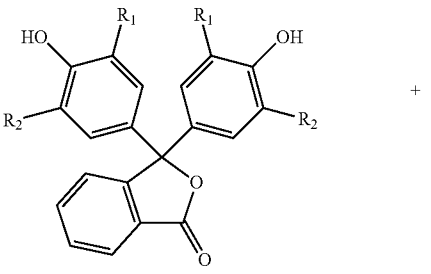

Compound-1

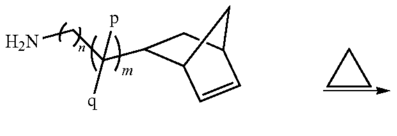

Compound-2

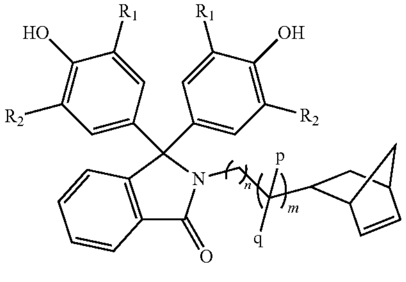

Formula-I wherein, $R_1$ and $R_2$ are selected from the group comprising of H, $C_1$-$C_5$ substituted or unsubstituted, straight or branched alkyl, alkoxy; p and q are selected form the group comprising of H and F; m=0 or 1; n=0-6.

3. An aromatic polyester bearing pendant norbornenyl groups of formula (II) from the bisphenol bearing pendant clickable norbornenyl group of formula (I) as claimed in claim 1;

Formula (II)

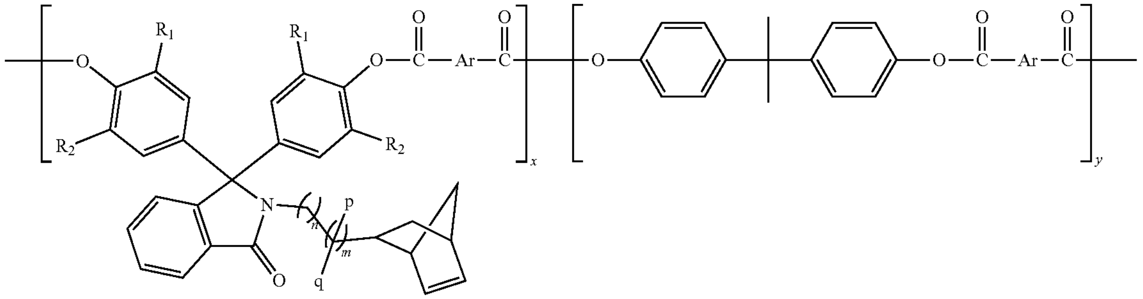

wherein, $R_1$ and $R_2$ are selected from a group comprising of H, $C_1$-$C_5$ substituted or unsubstituted, straight or branched alkyl, alkoxy; p and q are selected form a group comprising of H and F; m=0 or 1; n=0-6; wherein, x=0.1-1, and y=0-0.9; Ar=isophthaloyl chloride, terephthaloyl chloride, or mixtures thereof.

4. A process for the preparation of polyester of formula (II) as claimed in claim 3, wherein said process comprises the steps of:

a) dissolving monomer of formula (I) and bisphenol A in an alkali solution and stirring the reaction mixture;

b) adding benzyltriethylammonium chloride to the reaction mixture of step (a) and stirring followed by addition of a solution of diacid chloride in dichloromethane to the reaction mixture and stirring vigorously; and c) pouring the reaction mixture of step (b) into hot water; filtering the precipitated polymer and washing it several times with water followed by work-up to afford polyester of formula (II);

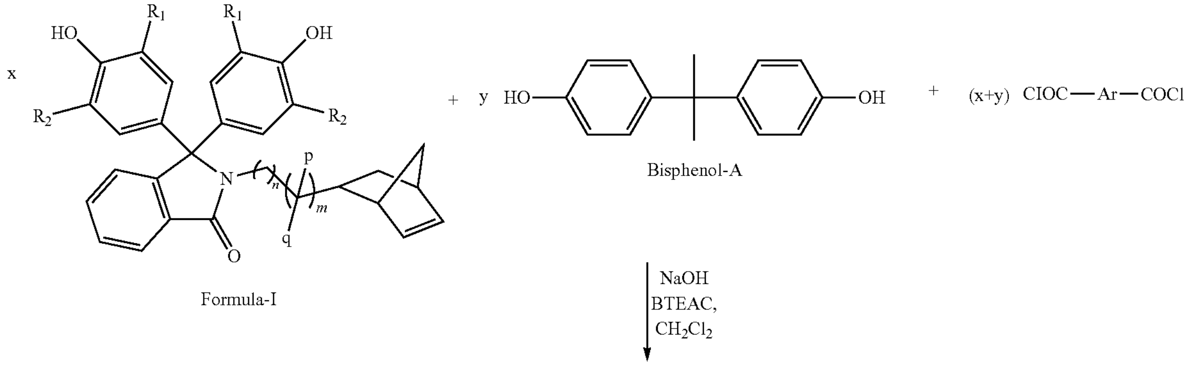

-continued

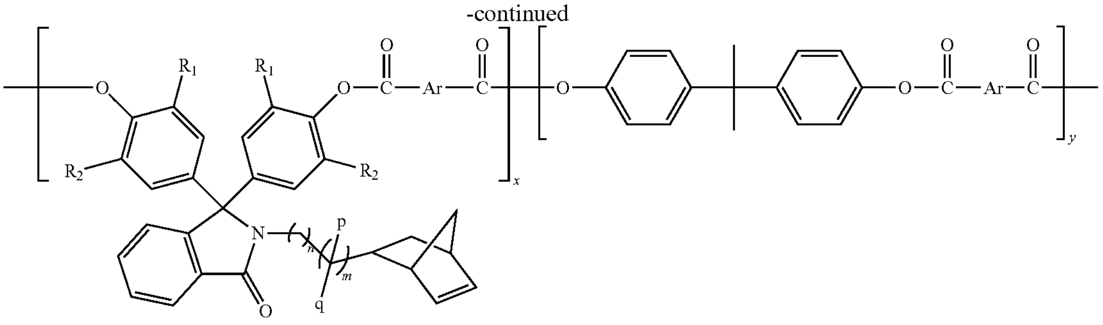

Formula (II)

wherein, $R_1$ and $R_2$ are selected from the group comprising of H, $C_1$-$C_5$ substituted or unsubstituted, straight or branched alkyl, alkoxy; p and q are selected form the group comprising of H and F; m=0 or 1; n=0-6; wherein, x=0.1-1, and y=0-0.9; Ar=isophthaloyl chloride, terephthaloyl chloride, or mixtures thereof.

5. The process as claimed in claim 4, wherein said diacid chloride is selected from isophthaloyl chloride, terephthaloyl chloride, or mixtures thereof.

6. The aromatic polyester bearing pendant norbornenyl groups of formula (II) as claimed in claim 3, wherein said polymer is cross-linked thermally or photochemically.

7. The aromatic polyester bearing pendant norbornenyl groups of formula (II) as claimed in claim 3, wherein said polymer are capable of undergoing tetrazine-norbornene inverse electron demand Diels-Alder reaction, photoinitiated thiol-norbornene reaction or metal-free azide-norbornene 1,3-dipolar cycloaddition click reaction to form modified polymers.

* * * * *